United States Patent
Smith et al.

(10) Patent No.: US 11,162,921 B2
(45) Date of Patent: Nov. 2, 2021

(54) METHOD FOR EXTRACTING PHARMACOGENETIC DNA FROM BIOLOGICAL FLUID RETAINED IN A SOLID RESIN COLLECTION DEVICE

(71) Applicant: Alcala Pharmaceutical, Inc., San Diego, CA (US)

(72) Inventors: David J. Smith, San Diego, CA (US); Christian Tagwerker, Oceanside, CA (US); Matthew D. Rifat, San Diego, CA (US)

(73) Assignee: ALCALA PHARMACEUTICAL, INC., San Diego, CA (US)

( * ) Notice: Subject to any disclaimer, the term of this patent is extended or adjusted under 35 U.S.C. 154(b) by 0 days.

(21) Appl. No.: 16/820,540

(22) Filed: Mar. 16, 2020

(65) Prior Publication Data

US 2020/0309742 A1 Oct. 1, 2020

Related U.S. Application Data

(60) Provisional application No. 62/827,634, filed on Apr. 1, 2019.

(51) Int. Cl.
*G01N 30/06* (2006.01)
(52) U.S. Cl.
CPC ....... *G01N 30/06* (2013.01); *G01N 2030/062* (2013.01); *G01N 2030/065* (2013.01)
(58) Field of Classification Search
CPC .............. C12N 15/1003; C12Q 1/6806; C12Q 2523/301; G01N 2030/062
See application file for complete search history.

(56) References Cited

U.S. PATENT DOCUMENTS 6,974,706 B1 12/2005 Melker et al.
7,815,803 B2 10/2010 Kobold et al.
(Continued)

FOREIGN PATENT DOCUMENTS

WO WO2017157650 A1 9/2017
WO WO2018093724 A1 5/2018

OTHER PUBLICATIONS

Cao, Zhenning et al—"A Microfluidic Device with Integrated Sonication and Immunoprecipitation for Sensitive Epigenetic Assays"—Analytical Chemistry, 2016 (Year: 2016).*

(Continued)

*Primary Examiner* — Bradley R Spies
(74) *Attorney, Agent, or Firm* — Roeder & Broder LLP; James P. Broder

(57) ABSTRACT

A method for extracting pharmacogenetic DNA from dried blood that is retained in a solid resin collection device includes one or more of the steps of combining the dried blood and at least a portion of the solid resin collection device in a first vessel, sonicating the first vessel containing the dried blood and at least a portion of the solid resin collection device, moving at least some of the contents of the first vessel including the portion of the solid resin collection device to a solid resin spin column, adding an elution buffer to the solid resin spin column, centrifuging the solid resin spin column so that at least some of the contents of the solid resin spin column are transferred to a second vessel, and processing the contents of the second vessel by conducting one of capillary electrophoresis, Next-Generation Sequencing, DNA sequencing or genotyping, and mass spectrometry-based sequencing on the contents of the second vessel.

21 Claims, 2 Drawing Sheets

(56) References Cited

U.S. PATENT DOCUMENTS

| | | | |
|---|---|---|---|
| 9,816,980 | B2 | 11/2017 | Cristoni et al. |
| 9,927,331 | B2 | 3/2018 | Zhang et al. |
| 10,088,460 | B2 | 10/2018 | DeWitte et al. |
| 10,262,112 | B2 | 4/2019 | Ryan |
| 10,739,321 | B2 | 8/2020 | DeWitte et al. |
| 2009/0203004 | A1* | 8/2009 | Sanderson ........... C12Q 1/6883 435/6.16 |
| 2013/0116597 | A1 | 5/2013 | Rudge et al. |
| 2018/0135128 | A1 | 5/2018 | Sanders et al. |
| 2018/0135135 | A1 | 5/2018 | Sanders et al. |
| 2018/0372697 | A1 | 12/2018 | DeWitte et al. |

OTHER PUBLICATIONS

Kanoatov, Mirzo et al—"Analysis of DNA in Phosphate Buffered Saline Using Kinetic Capillary Electrophoresis"—Analytical Chemistry, 2016 (Year: 2016).*

Diagenode—"Best Practices for DNA Shearing for NGS"—bitsizebio, 2017 (Year: 2017).*

Gruner, Nico et al—"Dried Blood Spots—Preparing and Processing for Use in Immunoassays and in Molecular Techniques"—Journal of Visualized Experiments, 2015 (Year: 2015).*

Pchelintsev, Nikolay et al—"Critical Parameters for Efficient Sonication and Improved Chromatin Immunoprecipitation of High Molecular Weight Proteins"—PLos One, 2016 (Year: 2016).*

Herrmann, M. et al—"A rapid and simple method for the isolation of apoptotic DNA fragments"—Nucleic Acids Research, 1994 (Year: 1994).*

El-Mogy, Mohamed et al—Total RNA/DNA Purification and Detection from Blood Preserved on a Neoteryx Mitra Microsampling Device—Application Note 83, Neoteryx Mitra Microsampling Device, Norgen Biotek Corp, 2016 (Year: 2016).*

Norgen Biotek Corp—DNA Purification from Blood Preserved on a Neoteryx Mitra Microsampling Device, Supplementary Protocol—2016 (Year: 2016).*

Agencourt DNAdvance Genomic DNA Isolation Kit. Agencourt Bioscience Corporation. www.agentcourt.com/technical and www.beckmancoulter.com/customersport/msds/msds.asp.

AppliedBiosystems, Isolation of DNA for Genotyping Experiments. Optimized for buccal swab samples using the Mag MAX DNA multi-Sample Ultra Kit. Thermo Fisher Scientific.

Sample & Assay Technologies. QIAprep Spin Miniprep Kit High-Yield Protocol. Qiagen.

PureLink Genomic DNA Kits. For Purification of genomic DNA. Invitrogen by Life Technologies.

* cited by examiner

METHOD FOR EXTRACTING PHARMACOGENETIC DNA FROM BIOLOGICAL FLUID RETAINED IN A SOLID RESIN COLLECTION DEVICE

RELATED APPLICATION

This application claims priority on U.S. Provisional Application Ser. No. 62/827,634, filed on Apr. 1, 2019, and entitled "METHOD FOR EXTRACTING PHARMACOGENETIC DNA FROM DRIED BLOOD RETAINED IN VOLUMETRIC ABSORPTIVE MICRO SAMPLING DEVICE". To the extent permitted, the contents of U.S. Provisional Application Ser. No. 62/827,634, are incorporated in their entirety herein by reference.

BACKGROUND

The ability to identify the presence or absence of specific mutations in certain genes, whose respective gene products play a role in pharmacogenetic (PGx) interactions, metabolism, pharmacodynamics or pharmacokinetics, is vital in determining medication dosing guidelines for an individual patient. Current issues in effectively determining these types of mutations in conventional PGx testing include test panels with only a handful of genes (1-5) investigated at one time and low coverage of mutation sites due to low DNA yield, e.g. from a buccal swab (saliva specimen) or a whole blood venipuncture specimen, which offer reduced operational efficiencies in collecting the specimen. Specimen types and current extraction methods resulting in low DNA yield combined with minimal test panels lead to unnecessary re-collection, re-extraction and additional genotyping runs, which are not feasible for routine clinical laboratory or research testing in regards to costs and time equivalents consumed.

SUMMARY

The present invention is directed toward a method for extracting pharmacogenetic DNA from dried blood that is retained in a solid resin collection device. In certain embodiments, the method includes the step of combining the dried blood and at least a portion of the solid resin collection device in a first vessel.

In various embodiments, the step of combining can also include adding a phosphate buffered saline solution into the first vessel.

In some embodiments, the method can also include the step of sonicating the first vessel including the dried blood and at least a portion of the solid resin collection device. In certain such embodiments, the step of sonicating can include sonicating the first vessel for at least approximately 10 seconds and less than approximately 5 minutes, or for at least approximately 30 seconds and less than approximately two minutes.

In various embodiments, the step of sonicating can include alternating the sonication pulsing on and off. In some such embodiments, the step of sonicating can include cyclically alternating the sonication pulsing on for approximately 20 seconds and off for approximately 10 seconds.

In certain embodiments, the method also includes the step of moving at least some of the contents of the first vessel to a solid resin spin column. In some such embodiments, the step of moving includes moving the portion of the solid resin collection device to the solid resin spin column.

In various embodiments, the method can also include the step of adding one or more wash buffers to the solid resin spin column.

In some embodiments, the method can also include the step of adding an elution buffer to the solid resin spin column.

In certain embodiments, the method can include the step of centrifuging the solid resin spin column so that at least some of the contents of the solid resin spin column are transferred to a second vessel.

In various embodiments, the method can include the step of processing the contents of the second vessel by conducting one of capillary electrophoresis, Next-Generation Sequencing, DNA sequencing or genotyping, and mass spectrometry-based sequencing on the contents of the second vessel.

In some embodiments, the method can include the step of adding a magnetic bead solution/slurry to the contents of the first vessel.

The present invention is also directed toward a method for extracting pharmacogenetic DNA from dried blood that is retained in a solid resin collection device. In some embodiments, the method can include the steps of combining the dried blood and at least a portion of the solid resin collection device in a first vessel, and moving at least some of the contents of the first vessel to a solid resin spin column.

In certain embodiments, the step of moving includes moving the portion of the solid resin collection device to the solid resin spin column.

In various embodiments, the method can include the step of adding one or more wash buffers to the solid resin spin column.

In some embodiments, the method can include the step of adding an elution buffer to the solid resin spin column.

In certain embodiments, the method can include the step of centrifuging the solid resin spin column so that at least some of the contents of the solid resin spin column are transferred to a second vessel.

In various embodiments, the method can include the step of processing the contents of the second vessel by conducting one of capillary electrophoresis, Next-Generation Sequencing, DNA sequencing or genotyping, and mass spectrometry-based sequencing on the contents of the second vessel.

The present invention is also directed toward a method for extracting pharmacogenetic DNA from dried blood that is retained in a solid resin collection device. In certain embodiments, the method includes the steps of combining the dried blood and at least a portion of the solid resin collection device in a first vessel; sonicating the first vessel containing the dried blood and at least a portion of the solid resin collection device; moving at least some of the contents of the first vessel including the portion of the solid resin collection device to a solid resin spin column; adding an elution buffer to the solid resin spin column; centrifuging the solid resin spin column so that at least some of the contents of the solid resin spin column are transferred to a second vessel; and processing the contents of the second vessel by conducting one of capillary electrophoresis, Next-Generation Sequencing, DNA sequencing or genotyping, and mass spectrometry-based sequencing on the contents of the second vessel.

BRIEF DESCRIPTION OF THE DRAWING

The novel features of this invention, as well as the invention itself, both as to its structure and its operation, will be best understood from the accompanying figure, taken in FIG. 1 is a flow chart showing one embodiment of a method for extracting pharmacogenetic DNA from a biological fluid retained in a solid resin collection device and/or determining the presence or absence of a pharmacogenetic marker in the pharmacogenetic DNA.

Figure 1:
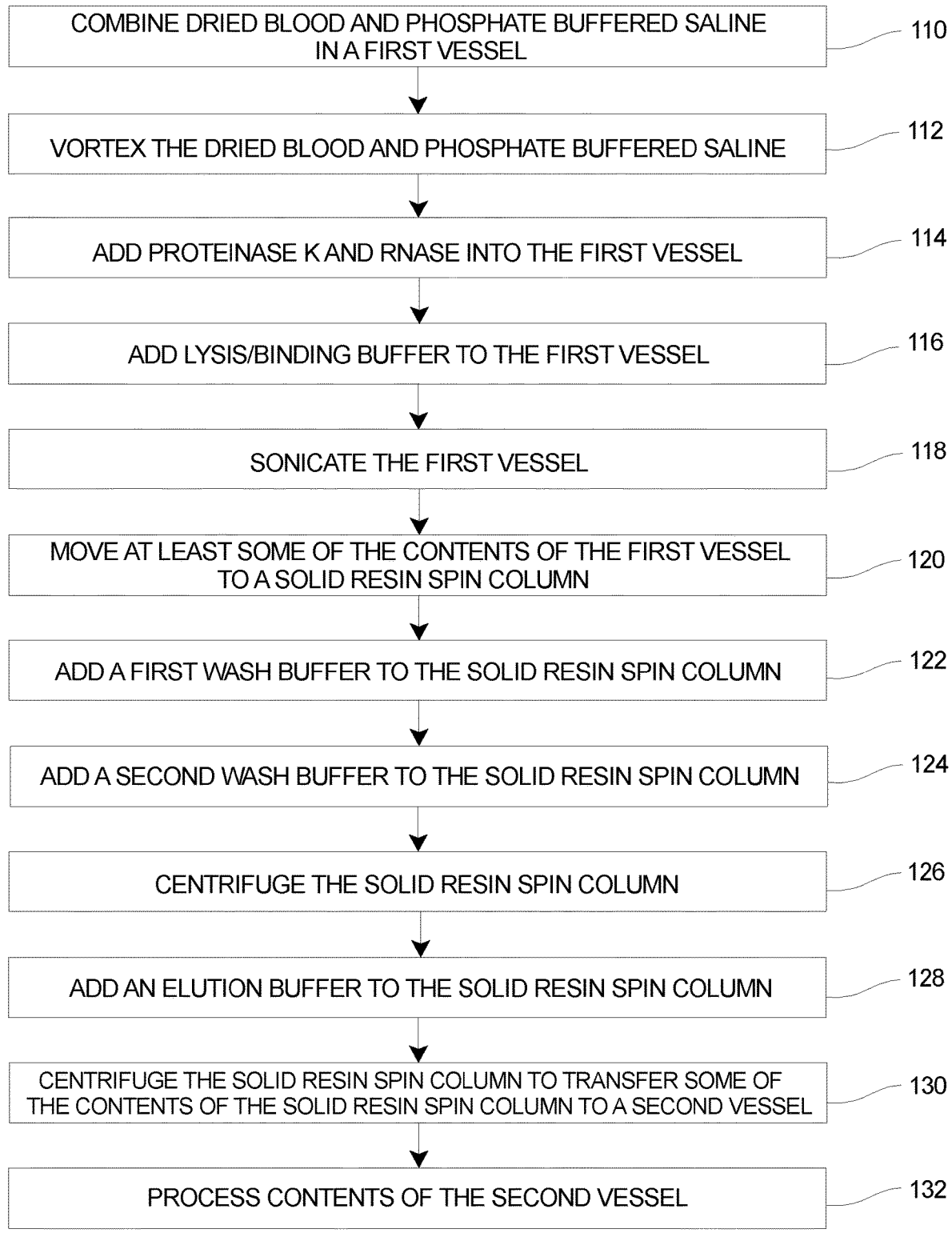

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DESCRIPTION

Embodiments of the present invention are described herein in the context of a method for extracting pharmacogenetic DNA from dried blood retained in a solid resin collection device and/or determining the presence or absence of a pharmacogenetic marker in the pharmacogenetic DNA. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Further, it is recognized that other suitable biological samples can equally and effectively be analyzed utilizing one or more of the methods disclosed herein. These other biological samples can include, without limitation, urine, whole blood, blood plasma, serum, saliva (oral fluids), cerebrospinal fluid (CSF), tears, sweat, synovial fluid, semen, feces, etc. Additionally, the types of "dried blood samples" can vary, and can include, without limitation, whole blood samples obtained via Neoteryx® blood collection devices such as a Mitra® tip or other suitable solid resin collection devices, as non-exclusive examples. It is understood that these types of solid resin collection devices can be sized and/or configured as required to retain a desired volume of dried blood. For example, in certain embodiments herein, the solid resin collection device is configured to retain no greater than approximately 50 µL, 30 µL, 20 µL or 10 µL of whole blood which is then dried on and/or within the solid resin collection device.

As used herein, for the sake of simplicity, the term "pharmacogenetic marker", can include, but in one embodiment, is not limited to any or all of the following 141 single nucleotide polymorphism or InDel (Insertion/Deletion) loci and their respective rsIDs and alleles, copy number variations (CNVs) and/or two gender probes. In another embodiment, the pharmacogenetic marker is limited to the following 141 single nucleotide polymorphism or InDel (Insertion/Deletion) loci and their respective rsIDs and alleles, copy number variations (CNVs) and/or two gender probes. Specifically, the following 141 variants were to be determined among 23 genes, including 2 gender probes, as indicated in the Tables below:

| Gene | Name | Locus | Major Allele | Minor Allele | Haplotypes |
|---|---|---|---|---|---|
| ADRA2A | rs1800544 | chr10: 112836503-112836503 | G | C | |
| CES1 | rs71647871 | chr16: 55857570-55857570 | C | T | |
| COMT | rs4680 | chr22: 19951271-19951271 | G | A | |
| CYP1A2 | rs12720461 | chr15: 75041351-75041351 | C | T | *1K |
| CYP1A2 | rs2069514 | chr15: 75038220-75038220 | G | A | *1C, *1L |
| CYP1A2 | rs2069526 | chr15: 75041341-75041341 | T | G | *1E, *1J, *1K, *1W, *1G |
| CYP1A2 | rs2470890 | chr15: 75047426-75047426 | C | T | *1B, *1L, *1G |
| CYP1A2 | rs35694136 | chr15: 75039612-75039613 | AT | A | *1D, *1L, *1V, *1W |
| CYP1A2 | rs4646425 | chr15: 75043281-75043281 | C | T | |
| CYP1A2 | rs4646427 | chr15: 75045692-75045692 | T | C | |
| CYP1A2 | rs762551 | chr15: 75041917-75041917 | C | A | *1F, *1J, *1K, *1L, *1V, *1W |
| CYP1A2 | rs56107638 | chr15: 75045612-75045612 | G | A | *7 |
| CYP2C19 | rs4244285 | chr10: 96541616-96541616 | G | A | *2 |
| CYP2C19 | rs4986893 | chr10: 96540410-96540410 | G | A | *3 |
| CYP2C19 | rs28399504 | chr10: 96522463-96522463 | A | G | *4, *4B |
| CYP2C19 | rs56337013 | chr10: 96612495-96612495 | C | T | *5 |
| CYP2C19 | rs72552267 | chr10: 96535210-96535210 | G | A | *6 |
| CYP2C19 | rs72558186 | chr10: 96541756-96541756 | T | A | *7 |
| CYP2C19 | rs41291556 | chr10: 96535173-96535173 | T | C | *8 |
| CYP2C19 | rs17884712 | chr10: 96535246-96535246 | G | A | *9 |
| CYP2C19 | rs6413438 | chr10: 96541615-96541615 | C | T | *10 |
| CYP2C19 | rs55640102 | chr10: 96612671-96612671 | A | C | *12 |
| CYP2C19 | rs12248560 | chr10: 96521657-96521657 | C | T | *17 |

-continued

| Gene | rsID | Location | Ref | Alt | Alleles |
|---|---|---|---|---|---|
| CYP2C19 | rs55752064 | chr10: 96522512-96522512 | T | C | *14 |
| CYP2C19 | rs17882687 | chr10: 96522517-96522517 | A | C | *15 |
| CYP2C19 | rs58973490 | chr10: 96535264-96535264 | G | A | |
| CYP2C19 | rs118203759 | chr10: 96612542-96612542 | C | G | |
| CYP2C9 | rs1799853 | chr10: 96702047-96702047 | C | T | *2 |
| CYP2C9 | rs1057910 | chr10: 96741053-96741053 | A | C | *3 |
| CYP2C9 | rs28371686 | chr10: 96741058-96741058 | C | G | *5 |
| CYP2C9 | rs9332130 | chr10: 96709037-96709037 | A | G | |
| CYP2C9 | rs9332131 | chr10: 96709038-96709039 | GA | G | *6 |
| CYP2C9 | rs7900194 | chr10: 96702066-96702066 | G | A | *8 |
| CYP2C9 | rs7900194 | chr10: 96702066-96702066 | G | T | *27 |
| CYP2C9 | rs28371685 | chr10: 96740981-96740981 | C | T | *11 |
| CYP2C9 | rs72558189 | chr10: 96701991-96701991 | G | A | *14 |
| CYP2C9 | rs1799853 | chr10: 96702047-96702047 | C | T | *2 |
| CYP2C9 | rs1057909 | chr10: 96741051-96741051 | A | G | |
| CYP2C9 | rs67807361 | chr10: 96698494-96698494 | C | A | *7 |
| CYP2C9 | rs56165452 | chr10: 96741054-96741054 | T | C | |
| CYP2D6 | rs16947 | chr22: 42523943-42523943 | A | G | *1, *3, *3B, *4, *4J, *4M, *6, *6C, *7, *9, *10, *15, *39, *49, *53, *33 |
| CYP2D6 | rs1135840 | chr22: 42522613-42522613 | G | C | *1, *3, *3B, *4J, *4M, *6, *7, *9, *15, *53, *33 |
| CYP2D6 | rs35742686 | chr22: 42524243-42524244 | CT | T | *3, *3B |
| CYP2D6 | rs1135824 | chr22: 42525044-42525044 | T | C | *3B |
| CYP2D6 | rs1065852 | chr22: 42526694-42526694 | G | A | *4, *4J, *4K, *10, *14A, *49 |
| CYP2D6 | rs3892097 | chr22: 42524947-42524947 | C | T | *4, *4J, *4K, *4M |
| CYP2D6 | rs5030655 | chr22: 42525085-42525086 | CA | C | *6, *6C |
| CYP2D6 | rs5030867 | chr22: 42523858-42523858 | T | G | *7 |
| CYP2D6 | rs5030865 | chr22: 42525035-42525035 | C | A | *8 |
| CYP2D6 | rs5030656 | chr22: 42524175-42524178 | CCTT | C | *9 |
| CYP2D6 | rs5030862 | chr22: 42526670-42526670 | C | T | *12 |
| CYP2D6 | rs5030865 | chr22: 42525035-42525035 | C | T | *14A, *14B |
| CYP2D6 | rs72549357 | chr22: 42526656-42526656 | C | CA | *15 |
| CYP2D6 | rs28371706 | chr22: 42525772-42525772 | G | A | *17 |
| CYP2D6 | rs59421388 | chr22: 42523610-42523610 | C | T | *29 |
| CYP2D6 | rs769258 | chr22: 42526763-42526763 | C | T | *35A |
| CYP2D6 | rs28371725 | chr22: 42523805-42523805 | C | T | *41 |
| CYP2D6 | rs28371696 | chr22: 42526717-42526717 | C | T | *46 |
| CYP2D6 | rs1135822 | chr22: 42525182-42525182 | A | T | *49, *53 |
| CYP2D6 | rs1135823 | chr22: 42525176-42525176 | C | A | *53 |
| CYP2D6 | rs61736512 | chr22: 42525134-42525134 | C | T | |
| CYP2D6 | rs28371717 | chr22: 42524310-42524310 | C | A | *33 |
| CYP2D6 | rs1135836 | chr22: 42522660-42522660 | A | G | *18 |
| CYP2D6 | rs267608319 | chr22: 42522751-42522751 | C | T | *31 |
| CYP2D6 | rs72549349 | chr22: 42523843-42523843 | C | G | *44 |
| CYP2D6 | rs28371705 | chr22: 42525798-42525798 | G | C | |
| CYP2D6 | rs201377835 | chr22: 42525912-42525912 | C | G | *11 |
| CYP3A4 | rs12721627 | chr7: 99366093-99366093 | G | C | *16 |
| CYP3A4 | rs2242480 | chr7: 99361466-99361466 | C | T | *1G, *16B, *18B, *19 |
| CYP3A4 | rs12721629 | chr7: 99359800-99359800 | G | A | *12 |
| CYP3A4 | rs4987161 | chr7: 99366081-99366081 | A | G | *17 |
| CYP3A4 | rs55785340 | chr7: 99365983-99365983 | A | G | *2 |
| CYP3A4 | rs72552799 | chr7: 99367788-99367788 | C | T | *8 |
| CYP3A4 | rs67784355 | chr7: 99359829-99359829 | G | A | *11 |
| CYP3A4 | rs4986909 | chr7: 99359670-99359670 | G | A | *13 |
| CYP3A4 | rs35599367 | chr7: 99366316-99366316 | G | A | *22 |
| CYP3A4 | rs67666821 | chr7: 99355806-99355806 | G | GT | *20 |
| CYP3A4 | rs28371759 | chr7: 99361626-99361626 | A | G | *18A, *18B |
| CYP3A4 | rs55901263 | chr7: 99365994-99365994 | G | C | *5 |
| CYP3A4 | rs3208361 | chr7: 99366070-99366070 | T | C | |
| CYP3A4 | rs55951658 | chr7: 99367825-99367825 | T | C | *4 |
| CYP3A5 | rs776746 | chr7: 99270539-99270539 | C | T | *1 |
| CYP3A5 | rs10264272 | chr7: 99262835-99262835 | C | T | *6 |
| CYP3A5 | rs15524 | chr7: 99245914-99245914 | A | G | *1D, *3, *3B, *3K |
| CYP3A5 | rs28365083 | chr7: 99250236-99250236 | G | T | *2 |
| CYP3A5 | rs28383468 | chr7: 99273815-99273815 | G | A | *3B |
| CYP3A5 | rs28383479 | chr7: 99258139-99258139 | C | T | *9 |
| CYP3A5 | rs41303343 | chr7: 99250393-99250393 | T | TA | *7 |
| CYP3A5 | rs55817950 | chr7: 99273821-99273821 | G | A | *8 |

-continued

| Gene | rsID | Location | Allele 1 | Allele 2 | Notes |
|---|---|---|---|---|---|
| CYP3A5 | rs28365085 | chr7: 99245974-99245974 | A | G | |
| CYP3A5 | rs56411402 | chr7: 99262860-99262860 | T | C | *4 |
| DRD1 | rs4532 | chr5: 174870150-174870150 | C | T | |
| DRD2 | rs1799978 | chr11: 113346351-113346351 | T | C | |
| DRD2 | rs2283265 | chr11: 113285536-113285536 | C | A | |
| DRD2 | rs6275 | chr11: 113283477-113283477 | A | G | |
| DRD2 | rs6277 | chr11: 113283459-113283459 | G | A | |
| F2 | rs1799963 | chr11: 46761055-46761055 | G | A | |
| F5 | rs6025 | chr1: 169519049-169519049 | T | C | |
| GNB3 | rs5443 | chr12: 6954875-6954875 | C | T | |
| HTR1A | rs10042486 | chr5: 63261329-63261329 | C | T | |
| HTR1A | rs6295 | chr5: 63258565-63258565 | C | G | |
| HTR2A | rs7997012 | chr13: 47411985-47411985 | A | G | |
| HTR2A | rs9316233 | chr13: 47433355-47433355 | C | G | |
| HTR2A | rs6313 | chr13: 47469940-47469940 | G | A | |
| HTR2A | rs6311 | chr13: 47471478-47471478 | C | T | |
| HTR2C | rs1414334 | chrX: 114138144-114138144 | C | G | |
| HTR2C | rs3813928 | chrX: 113818282-113818282 | G | A | |
| HTR2C | rs3813929 | chrX: 113818520-113818520 | C | T | |
| HTR2C | rs518147 | chrX: 113818582-113818582 | G | C | |
| HTR2C | rs6318 | chrX: 113965735-113965735 | G | C | |
| MTHFR | rs1801133 | chr1: 11856378-11856378 | G | A | |
| MTHFR | rs1801131 | chr1: 11854476-11854476 | T | G | |
| MTHFR | rs4846051 | chr1: 11854457-11854457 | G | A | |
| OPRM1 | rs1799971 | chr6: 154360797-154360797 | A | G | |
| OPRM1 | rs2281617 | chr6: 154487421-154487421 | C | T | |
| OPRM1 | rs510769 | chr6: 154362019-154362019 | C | T | |
| SLC6A2 | rs3785143 | chr16: 55695106-55695106 | C | T | |
| SLC6A2 | rs12708954 | chr16: 55731599-55731599 | C | A | |
| SLC6A4 | rs1042173 | chr17: 28525011-28525011 | A | G | |
| SLC6A4 | rs25531 | chr17: 28564346-28564346 | T | C | LA, LG |
| SLC6A4 | rs4795541 | chr17: 28564359-28564359 | A | Del | HTTLPR short form (S allele) |
| | | | | G or 43-44 nt Insertion | HTTLPR long form (L allele) |
| SLCO1B1 | rs4149056 | chr12: 21331549-21331549 | T | C | |
| SLCO1B1 | rs11045819 | chr12: 21329813-21329813 | C | A | |
| SLCO1B1 | rs2306283 | chr12: 21329738-21329738 | A | G | |
| SLCO1B1 | rs4149015 | chr12: 21283322-21283322 | G | A | |
| SLCO1B1 | rs4149081 | chr12: 21378021-21378021 | G | A | |
| SLCO1B1 | rs11045879 | chr12: 21382619-21382619 | T | C | |
| SLCO1B1 | rs2306282 | chr12: 21329802-21329802 | A | G | |
| SLCO1B1 | rs72559745 | chr12: 21329817-21329817 | A | G | |
| SLCO1B1 | rs72559746 | chr12: 21331606-21331606 | T | G | |
| SLCO1B1 | rs2291075 | chr12: 21331625-21331625 | C | T | |
| SLCO1B1 | rs4149057 | chr12: 21331599-21331599 | C | T | |
| VKORC1 | rs9923231 | chr16: 31107689-31107689 | C | T | |
| VKORC1 | rs9934438 | chr16: 31104878-31104878 | G | A | |
| VKORC1 | rs17708472 | chr16: 31105353-31105353 | G | A | |
| VKORC1 | rs2359612 | chr16: 31103796-31103796 | A | G | |
| VKORC1 | rs7294 | chr16: 31102321-31102321 | C | T | |
| VKORC1 | rs8050894 | chr16: 31104509-31104509 | C | G | |
| VKORC1 | rs11540137 | chr16: 31102324-31102324 | G | T | |
| VKORC1 | rs13337470 | chr16: 31105392-31105392 | G | T | |
| VKORC1 | rs2884737 | chr16: 31105554-31105554 | C | A | |

| Gender Probes Probe | Max Depth Limit |
|---|---|
| SRY::2655000-2655276 | <300 = female, >300 = male |
| USP9Y::14821246-14821410 | <50 = female, >50 = male |

FIG. 1 is a flow chart showing one embodiment of a method for extracting pharmacogenetic DNA from a biological fluid (such as dried blood in one non-exclusive embodiment) retained in a solid resin collection device and/or determining the presence or absence of a pharmacogenetic marker in the pharmacogenetic DNA. The dried blood sample (or other biological samples) can come from patients under the care of a treating physician from clinics and clinical institutions or from private parties. It is recognized that in certain embodiments, various steps illustrated and described with respect to the Figures herein can be omitted without deviating from the scope of the disclosure herein. It is further recognized that in some embodiments, additional steps can be included in the method shown in the Figures herein that are not illustrated and described. Additionally, it is understood that although dried blood is the biological sample that is specifically described relative to the description of the Figures herein, any other suitable biological samples could equally be utilized. In other words, as used herein, "dried blood" is but one example of the "biological sample". In certain non-exclusive embodiments, the method for extracting pharmacogenetic DNA from dried blood retained in a solid resin collection device can include one or more of the following steps. It should also be noted that pharmacogenetic RNA can equally be extracted utilizing the methods disclosed herein, with slight variations to the method as described herein.

At step 110, the solid resin collection device containing dried blood is combined in a first vessel with phosphate buffered saline (PBS). The volume and/or pH of the phosphate buffered saline can vary as needed. In one embodiment, approximately 50-500 μL of PBS can be added. In another embodiment, approximately 200 μL of PBS can be added. The pH of the PBS can be approximately 7.4. Alternatively, the pH of the PBS can be higher or lower than 7.4.

At step 112, the contents of the first vessel can be vortexed. The duration and extent of the vortexing can vary. In one embodiment, the first vessel can be vortexed at the highest setting for between 30 seconds and five minutes. Alternatively, the first vessel can be vortexed for approximately one minute. Still alternatively (or additionally), the first vessel can be vortexed at a lower setting.

At step 114, Proteinase K and RNase (such as RNase A, in one non-exclusive example) can be added to the first vessel. The amounts and/or concentrations of Proteinase K and/or RNase that are added can be varied. In one embodiment, approximately 20 μL of Proteinase K and approximately 20 μL of RNase can be added to the first vessel. Alternatively, greater or less than 20 μL of Proteinase K and/or greater or less than 20 μL of RNase can be added to the first vessel. The concentration of Proteinase K can vary within the range of 1 μg/mL to 100 mg/mL. Alternatively, the concentration of Proteinase K can be within the range of 1 μAU to 10,000 mAU. The concentration of RNase can be within the range of 1 μg/mL to 100 mg/mL. Alternatively, the concentration of RNase can be concentration that is greater than 1 U/mg protein or 1 Kunitz unit/mg protein. Still alternatively, DNase can be substituted for RNase at this step during extraction of RNA rather than DNA.

At step 116, a lysis/binding buffer is added to the first vessel. The type and volume of lysis/binding buffer that is added to the first vessel can be varied. In one embodiment, approximately 200 μL of the lysis/binding buffer can be added to the first vessel. Following addition of the lysis/binding buffer, the first vessel can be vortexed. The duration and extent of the vortexing can vary. In one embodiment, the first vessel can be vortexed at the highest setting for between 30 seconds and five minutes. Alternatively, the first vessel can be vortexed for approximately one minute. Still alternatively (or additionally), the first vessel can be vortexed at a lower setting. Following vortexing, the first vessel can be incubated at approximately 55° C. for between 30 minutes and 18 hours.

At step 118, the first vessel can be sonicated. In one embodiment, the sonication can occur at a 25% amplitude. Alternatively, the sonication can occur at greater than or less than 25% amplitude, such as between the range of 5-50% amplitude. Further, the sonication of the first vessel can be pulsed on and off during the sonication step. In one embodiment, the total length of time of the sonication can be between the range of approximately 10 seconds to five minutes. In another embodiment, the sonication can occur for approximately 30 seconds to two minutes. In yet another embodiment, the sonication can occur for approximately one minute. Sonication can be cyclically pulsed on for approximately 5-30 seconds, and then pulsed off for approximately 2-15 seconds, repeating this cycle for the duration of the sonication. In one embodiment, sonication is cyclically pulsed on for approximately 20 seconds and pulsed off for approximately 10 seconds during the sonication process.

The described sonication steps allow for shearing of genomic DNA into fragment sizes ranging from within the range of approximately 10,000 to approximately 50,000 basepairs (bp). By sonicating in the above-described manner, DNA fragments above or below the foregoing size range are reduced. The 10,000-50,000 bp DNA fragment sizes are desirable for DNA sequencing or genotyping for pharmacogenetic DNA targets. In order to sequence or genotype, an initial polymerase chain reaction (PCR) step is required to amplify the extracted DNA using specific primers designed for the sequencing or genotyping procedure. Sequencing or genotyping PCR primers anneal to the fragmented genomic DNA in order to amplify specific regions of the desired target DNA to determine specific mutations. These specific regions are referred to as amplicons. The sonication steps outlined above were found to specifically generate fragment sizes in the 10,000-50,000 bp range, which is particularly useful for the first sequencing or genotyping PCR step for interrogating pharmacogenetic DNA target regions or amplicons. Following sonication, ethanol or another solvent can be added to the first vessel.

At step 120, at least some of the contents of the first vessel can be moved to a solid resin spin column. In one embodiment, the contents of the first vessel that can be moved to the solid resin spin column can include at least a portion of the solid resin collection device, which can float above the column resin.

At step 122, a first wash buffer can be added to the solid resin spin column. The volume and type of the first wash buffer can vary. In various embodiments, the volume of the first wash buffer can be between approximately 200-500 μL. In one such embodiment, the volume of the first wash buffer that is added to the solid resin spin column is approximately 300 μL.

At step 124, a second wash buffer can be added to the solid resin spin column. The volume and type of the second wash buffer can vary. In one embodiment, the first wash buffer is different than the second wash buffer. In various embodiments, the volume of the second wash buffer can be between approximately 200-500 μL. In one such embodiment, the volume of the second wash buffer that is added to the solid resin spin column is approximately 300 μL.

At step 126, the solid resin spin column can be centrifuged. In various embodiments the centrifuging can occur after step 122, after step 124, or after both step 122 and step 124.

At step 128, an elution buffer is added to the solid resin spin column. The volume and type of the elution buffer than is added can be varied. In certain embodiments, the volume of the elution buffer that is added to the solid resin spin column can be in the range of approximately 1-1000 μL. In one such embodiment, the volume of the elution buffer that is added can be approximately 50 μL. Alternatively, ultrapure distilled water, DNase and/or RNase-Free can be substituted for the elution buffer.

At step 130, the solid resin spin column can be centrifuged to transfer at least some of the contents (isolated pharmacogenetic DNA) of the solid resin spin column to a second vessel.

Applying the solid resin spin column wash (steps 122 and/or 124) and elution procedure (step 128) including the original solid resin tip from the collection device which retains the sonicated, specifically fragmented DNA at this step, better cleanses or purifies the genomic DNA fragments from contamination which can include one or more of: cell debris, proteins, RNA, lipids, etc. Further, applying the solid resin spin column wash and elution procedure including the original solid resin tip from the solid resin collection device which retains the sonicated, specifically fragmented DNA can better dispose of DNA fragments having fewer than 10,000 bp. Such DNA fragments can adversely interfere with a first PCR step of any subsequent DNA sequencing or genotyping procedure.

In certain embodiments, wash buffers containing ethanol, isopropanol or guanidium thiocyanate effectively elute these contaminants from the solid resins while the desired DNA fragments in the 10,000-50,000 bp size range are retained. In some embodiments, an elution buffer with pH>8.0, e.g. 10 mM Tris-HCl, pH 9.0, 0.1 mM EDTA (as one non-exclusive example) or alternatively pure water with pH>8.0 (as another non-exclusive example) can be used in volumes ranging from 1-1000 microliters (4) to elute, i.e. collect, the DNA fragments from the solid resin into a collection vessel attached to the spin column by centrifugation. The eluted fraction of fragmented DNA in the 10,000-50,000 bp is better suited for sequencing/genotyping utilizing first step PCR procedures resulting in higher confidence pass rates for sequencing/genotyping experiments/tests and lower rejection rates based on analytical quality scores utilized to interpret the subsequent pharmacogenetic DNA mutations with clinical consequences.

At step 132, the contents of the second vessel can be processed in various ways. At step 132, the pharmacogenetic DNA is suitable for polymerase chain reaction (PCR), restriction enzyme digestion, Southern blotting, DNA sequencing, genotyping and/or any other suitable process known to those skilled in the art. By way of example, and not by way of limitation, DNA sequencing can be performed by capillary electrophoresis (CE) platforms, High Resolution Melt Curve (HRM) assays, probe-based or real-time PCR (qPCR)-based genotyping methods (e.g. TaqMan®, TaqMan® OpenArray® or Microarray), TruSeq Amplicon (TSCA) or AmpliSeq library preparation combined with or any type of Next-Generation Sequencing (NGS) platforms, and/or mass spectrometry-based sequencing methods such as by using MassARRAY® by Agena Bioscience. Alternatively, any other suitable method known to those skilled in the art can be utilized. This panel focuses on deeper sequencing of difficult targets (e.g. CYP2D6) and other Cytochrome gene SNPs but also includes SLC6A4 (as one non-exclusive example), an important gene when reporting on SSRI medication dosing guidelines. With the methods provided herein, any or all of the 141 single nucleotide polymorphism or InDel (Insertion/Deletion) loci and their respective rsIDs and alleles, and/or two gender probes can be identified.

Figure 2:
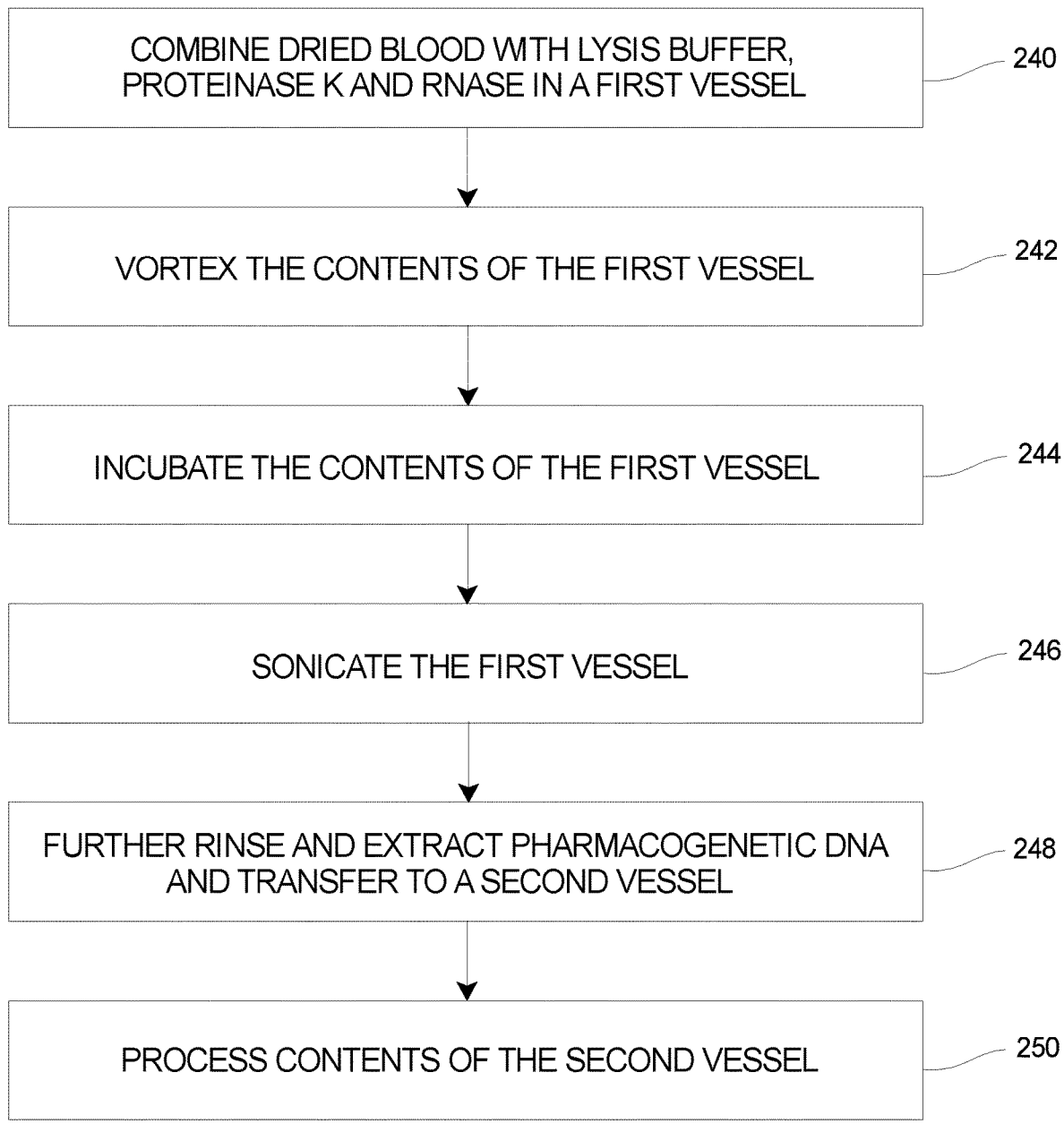
FIG. 2 is a flow chart showing another embodiment of a method for extracting pharmacogenetic DNA from a biological fluid retained in the solid resin collection device and/or determining the presence or absence of a pharmacogenetic marker in the pharmacogenetic DNA.

FIG. 2 is a flow chart showing another embodiment of a method for extracting pharmacogenetic DNA from a biological sample (such as dried blood in one non-exclusive embodiment) retained in a solid resin collection device and/or determining the presence or absence of a pharmacogenetic marker in the pharmacogenetic DNA.

At step 240, the solid resin collection device containing dried blood is combined in a first vessel with a lysis buffer, Proteinase K and RNase. The amounts, ratios and/or types of the lysis buffer, Proteinase K and/or RNase that are added can be varied. In various embodiments, the ratio of the volumes of the lysis buffer, Proteinase K and RNase can be approximately 97:2:1. In non-exclusive alternative embodiments, the ratio of the volumes of the lysis buffer, Proteinase K and RNase can be in the ranges of approximately 90-98: 1-8:1-5. In another embodiment, the ratio of the volumes of the lysis buffer, Proteinase K and RNase can be outside of the foregoing ranges. In certain embodiments, the total volume of the lysis buffer, Proteinase K and RNase can be within the range of approximately 50-500 µL. In one such embodiment, the total volume of the lysis buffer, Proteinase K and RNase that is added to the first vessel can be approximately 200 µL.

At step 242, the contents of the first vessel can be vortexed. The duration and extent of the vortexing can vary. In one embodiment, the first vessel can be vortexed at the highest setting for between 30 seconds and five minutes. Alternatively, the first vessel can be vortexed for approximately one minute. Still alternatively (or additionally), the first vessel can be vortexed at a lower setting.

At step 244, the first vessel can be incubated at approximately 55° C. for between 30 minutes and 18 hours.

At step 246, the first vessel can be sonicated. In one embodiment, the sonication can occur at a 25% amplitude. Alternatively, the sonication can occur at greater than or less than 25% amplitude, such as between the range of 5-50% amplitude. Further, the sonication of the first vessel can be pulsed on and off during the sonication step. In one embodiment, the total length of time of the sonication can be between the range of 10 seconds to two minutes. Sonication can be cyclically pulsed on for 5-30 seconds, and then pulsed off for 2-15 seconds for the entire duration of the sonication. In one embodiment, sonication is cyclically pulsed on for approximately 20 seconds and pulsed off for approximately 10 seconds during the sonication process. Following sonication, ethanol or another solvent can be added to the first vessel.

At step 248, the contents of the first vessel can be further rinsed to extract pharmacogenetic DNA. The manner for rinsing and extracting the pharmacogenetic DNA can vary. In one non-exclusive embodiment, magnetic beads can be used (as known to those skilled in the art). For example, in one embodiment, a magnetic bead slurry can be used. Magnetic beads can be used for downstream applications such as Agarose gel analysis, PCR amplification, restriction enzyme digestion, membrane hybridizations (e.g. Southern and dot/slot blots) AFLP, RFLP, RAPD, microsatellite and SNP analyses (for genotyping, fingerprinting, etc.), DNA sequencing and genotyping. In one representative, non-exclusive embodiment, after addition of the lysis buffer, RNAse A and Proteinase K incubation can be followed by removing the solid resin from the solid resin collection device stylus with sterilized tweezers, placing it in a sterile, round-bottom 2-mL microcentrifuge tube/vessel, adding 200 µL (50-500 uL) lysis Master Mix and vortexing the tip on highest setting (10) for 1 minute (30 sec-5 minutes). The 2 mL vessel with the cell suspension in the water bath can be incubated for at least approximately one hour upon which a magnetic bead solution/slurry is added to equilibrate at room temperature for approximately 15-20 minutes.

Sonication can then be carried out as described herein with the solid resin from the solid resin collection device and the lysis buffer. The vessel with cell material/solid resin suspension can be briefly centrifuged to collect the lysate and transfer of 50 µL cell suspension per well to a fresh 96-well plate carried out by micro pipetting. Further steps can include repeated wash buffer additions, incubations and removal (Bind 1/Bind 2 buffer/ethanol solutions) and finally addition of approximately 1-1000 µL of an elution buffer to collect the fragmented DNA (also see step 248 described herein). The pharmacogenetic DNA can then be transferred to a second vessel.

It is understood that the specific methodology disclosed herein regarding step 248 is intended to provide but one representative example of how to carry out this step. This example is not intended to be limiting in any manner, and it is recognized that an infinite number of other volumes, settings, time durations, etc., can be substituted for the specifics provided herein.

At step 250, the contents of the second vessel can be processed in various ways. At step 250, the pharmacogenetic DNA is suitable for polymerase chain reaction (PCR), restriction enzyme digestion, Southern blotting, DNA sequencing and/or any other suitable process known to those skilled in the art. By way of example, and not by way of limitation, DNA sequencing can be performed by capillary electrophoresis (CE) platforms, High Resolution Melt Curve (HRM) assays, probe-based or real-time PCR (quantitative PCR or qPCR)-based genotyping methods (e.g. TaqMan®, TaqMan® OpenArray® or Microarray), TruSeq Amplicon (TSCA) or AmpliSeq library preparation combined with or any type of Next-Generation Sequencing (NGS) platforms, and/or mass spectrometry-based sequencing methods such as by using MassARRAY® by Agena Bioscience. Alternatively, any other suitable method known to those skilled in the art can be utilized. This panel focuses on deeper sequencing of difficult targets (e.g. CYP2D6) and other Cytochrome gene SNPs but also includes SLC6A4 (as one non-exclusive example), an important gene when reporting on SSRI medication dosing guidelines. With the methods provided herein, any or all of the 141 single nucleotide polymorphism or InDel (Insertion/Deletion) loci and their respective rsIDs and alleles, copy number variations (CNVs) and/or two gender probes can be identified.

The present invention for extracting pharmacogenetic DNA from dried blood retained in a solid resin collection device allows certain volumes of whole blood/DNA to be collected resourcefully, leading to consistent DNA yields, applicable to PGx panels of over 20 pharmacogenes and thus more accurate and broader dosing guideline information, covering more medications for counseling of the individual patient and prevention of adverse drug reactions.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

As used herein, the recitation of numerical ranges by endpoints shall include all numbers subsumed within that range, inclusive (e.g., 2 to 8 includes 2, 2.1, 2.8, 5.3, 7, 8, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the method for extracting pharmacogenetic DNA from a biological sample retained in a solid resin collection device and/or determining the presence or absence of a pharmacogenetic marker in the pharmacogenetic DNA have been illustrated and described herein, one or more features of any one embodiment can be combined with one or more features of one or more of the other embodiments, provided that such combination satisfies the intent of the present invention.

Additionally, this method allows isolation of a very similar molecule to DNA-ribonucleic acid (RNA). RNA can conversely be isolated from the biological sample retained in a solid resin collection device using a column-based or non-column based extraction as described here (GITC-/TRIspin or Trizol based with or without hybridization with poly(dT) oligomers) by omitting RNase and mixing with deoxyribonuclease (DNase) instead. Subsequent RNA transcript analysis of pharmacogenes by RT-qPCR (reverse transcriptase quantitative PCR), Small RNA/non-coding RNA which may have a non-coding function (e.g., a ribosomal, microRNA or transfer RNA) sequencing, and/or Direct RNA Sequencing (DRSTM) technology and RNA-Seq is also possible.

While a number of exemplary aspects and embodiments of the method for extracting pharmacogenetic DNA from a biological sample retained in a solid resin collection device and/or determining the presence or absence of a pharmacogenetic marker in the pharmacogenetic DNA have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for extracting pharmacogenetic DNA from dried blood that is retained in a solid resin collection device, the method comprising the step of:
adding a portion of the solid resin collection device that retains the dried blood into a first vessel;
adding a lysis buffer into the first vessel;
and moving at least some of the contents of the first vessel including the portion of the solid resin collection device to a solid resin spin column.

2. The method of claim 1 further comprising the step of sonicating the first vessel including the dried blood and the portion of the solid resin collection device.

3. The method of claim 2 wherein the step of sonicating includes sonicating the first vessel for at least approximately 10 seconds and less than approximately 5 minutes.

4. The method of claim 2 wherein the step of sonicating includes sonicating the first vessel for at least approximately 30 seconds and less than approximately two minutes.

5. The method of claim 2 wherein the step of sonicating includes alternating the sonication pulsing on and off.

6. The method of claim 2 wherein the step of sonicating includes cyclically alternating the sonication pulsing on for approximately 20 seconds and off for approximately 10 seconds.

7. The method of claim 1 further comprising the step of adding one or more wash buffers to the solid resin spin column.

8. The method of claim 1 further comprising the step of adding an elution buffer to the solid resin spin column.

9. The method of claim 1 further comprising the step of centrifuging the solid resin spin column so that at least some of the contents of the solid resin spin column are transferred to a second vessel.

10. The method of claim 9 further comprising the step of processing the contents of the second vessel by conducting one of capillary electrophoresis, Next-Generation Sequencing, DNA sequencing or genotyping, and mass spectrometry-based sequencing on the contents of the second vessel.

11. The method of claim 1 further comprising the step of adding a magnetic bead solution/slurry to the contents of the first vessel.

12. A method for extracting pharmacogenetic DNA from dried blood that is retained in a solid resin collection device, the method comprising the steps of:
   adding a portion of the solid resin collection device that retains the dried blood into a first vessel;
   vortexing the first vessel containing the dried blood and the portion of the solid resin collection device;
   adding at least one of Proteinase K, RNase and DNase to the first vessel; and
   moving at least some of the contents of the first vessel including the portion of the solid resin collection device to a solid resin spin column.

13. The method of claim 12 further comprising the step of adding one or more wash buffers to the solid resin spin column.

14. The method of claim 12 further comprising the step of adding an elution buffer to the solid resin spin column.

15. The method of claim 12 further comprising the step of centrifuging the solid resin spin column so that at least some of the contents of the solid resin spin column are transferred to a second vessel.

16. The method of claim 15 further comprising the step of processing the contents of the second vessel by conducting one of capillary electrophoresis, Next-Generation Sequencing, DNA sequencing or genotyping, and mass spectrometry-based sequencing on the contents of the second vessel.

17. A method for extracting pharmacogenetic DNA from dried blood that is retained in a solid resin collection device, the method comprising the steps of:
   adding a portion of the solid resin collection device that retains the dried blood into a first vessel;
   sonicating the first vessel containing the dried blood and the portion of the solid resin collection device;
   moving at least some of the contents of the first vessel including the portion of the solid resin collection device to a solid resin spin column;
   adding an elution buffer to the solid resin spin column;
   centrifuging the solid resin spin column so that at least some of the contents of the solid resin spin column are transferred to a second vessel; and
   processing the contents of the second vessel by conducting one of capillary electrophoresis, Next-Generation Sequencing, DNA sequencing or genotyping, and mass spectrometry-based sequencing on the contents of the second vessel.

18. The method of claim 12 further comprising the step of adding a magnetic bead solution/slurry to the contents of the first vessel.

19. The method of claim 12 further comprising the step of sonicating the first vessel including the dried blood and the portion of the solid resin collection device.

20. The method of claim 19 wherein the step of sonicating includes sonicating the first vessel for at least approximately 10 seconds and less than approximately 5 minutes.

21. The method of claim 17 further comprising the step of adding a magnetic bead solution/slurry to the contents of the first vessel.

* * * * *